United States Patent
Guillot et al.

(10) Patent No.: US 7,179,636 B2
(45) Date of Patent: Feb. 20, 2007

(54) PREPARING A SAMPLE TO BE ANALYZED FROM A SAMPLE WITH VERY LARGE VOLUME

(75) Inventors: Emmanuelle Guillot, Saint Germain en Laye (FR); Laurence Durand-Bourlier, Clamart (FR); Stephane Bulteau, Lyons (FR)

(73) Assignee: Bio Merieux, Marcy l'Etoile (FR)

( * ) Notice: Subject to any disclaimer, the term of this patent is extended or adjusted under 35 U.S.C. 154(b) by 619 days.

(21) Appl. No.: 10/297,769

(22) PCT Filed: Jun. 8, 2001

(86) PCT No.: PCT/FR01/01786

§ 371 (c)(1),
(2), (4) Date: Mar. 20, 2003

(87) PCT Pub. No.: WO01/94527

PCT Pub. Date: Dec. 13, 2001

(65) Prior Publication Data

US 2003/0186428 A1    Oct. 2, 2003

(51) Int. Cl.
*C12N 1/02* (2006.01)

(52) U.S. Cl. .................. 435/261; 435/308.1; 435/34; 210/323.2; 210/767; 422/1

(58) Field of Classification Search ................ 435/261, 435/308.1, 34; 210/767, 323.2; 422/1
See application file for complete search history.

(56) References Cited

U.S. PATENT DOCUMENTS 4,547,289 A * 10/1985 Okano et al. ............... 210/652
6,635,179 B1 * 10/2003 Summerton et al. ........ 210/650

FOREIGN PATENT DOCUMENTS

GB       2339155 A * 1/2000

* cited by examiner

*Primary Examiner*—Leon B. Lankford, Jr.
(74) *Attorney, Agent, or Firm*—Oliff & Berridge, PLC

(57) ABSTRACT

The invention concerns the use of filtering means comprising a housing (2) wherein are arranged parallel to one another a plurality of hollow fibers (3), whereof the porous wall (3a) of each defines an aperture (4), so that said means comprises a inner path and an outer path (B) corresponding to the volume available between the fibers and the disc separator for treating an initial sample with large volume comprising in diluted state a plurality of micro-organisms of different sizes. The invention is characterised in that during at least a concentration step, one single means of filtering is available, the atomic mass unit threshold of the porous wall (3a) of the fibers is determined so as to retain the smallest micro-organism of the initial sample, said means being used in frontal mode and discontinuously, thereby providing the output sample liquid, that is the concentrate.

20 Claims, 1 Drawing Sheet

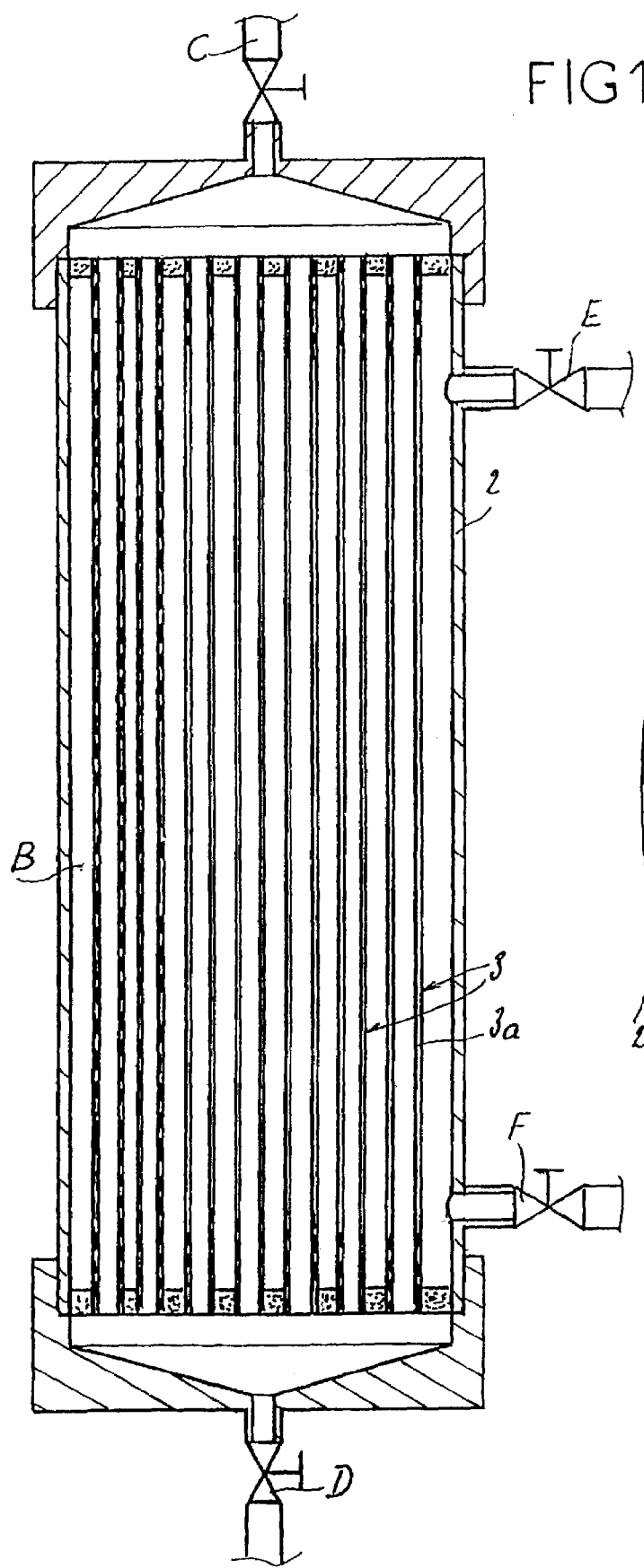
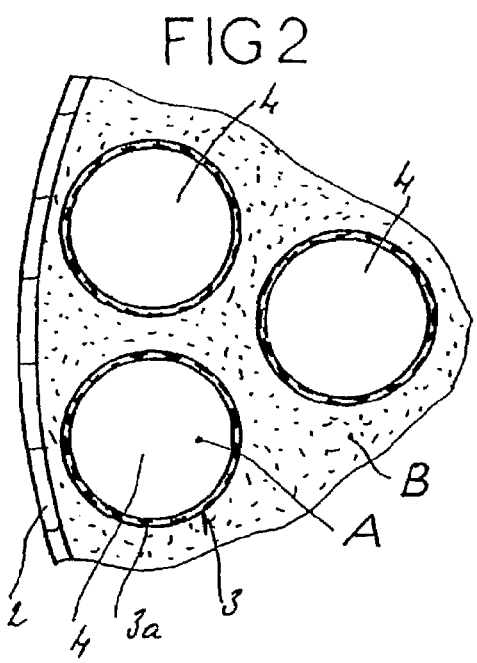

PREPARING A SAMPLE TO BE ANALYZED FROM A SAMPLE WITH VERY LARGE VOLUME

The invention relates to the field of the analysis of contaminants present in liquid media, which entails the treatment of large-volume samples containing, in the dilute state, a plurality of microorganisms of different sizes (viruses, bacteria, parasites) together with various organic or inorganic macromolecules to obtain a small-volume end liquid sample containing, in the concentrated state, practically the same relative composition of contaminants.

This contaminant, particularly microorganism, enrichment and the demand for small volumes for analysis are made necessary by the use of biochemical or biological analysis techniques, particularly immunoassays and molecular biology techniques, for example for multidetection.

Means of separating and concentrating microorganisms, particularly viruses, are known using adsorption for example. Aside from the fact that these means do not guarantee the viability of the microorganisms, they do not make it possible to obtain samples of a volume compatible with the analysis techniques mentioned above.

Other means employed for collecting microorganisms in liquid media call upon filtration methods and upon the analysis of just one type of microorganism but do not always allow quantitative results to be achieved.

Mention may for example be made, in the case of bacteria and parasites, of the use, according to the recommendations of standardized methods, of plane membranes with pores of sizes ranging between 0.2 µm and 1 µm depending on the species.

Known, particularly from FR-B-2693474, is a technique based on tangential ultrafiltration employing, in the conventional way, one or more membranes and allowing microorganisms of various sizes to be separated, while at the same time guaranteeing the viability of said microorganisms.

However, the demands placed on the volume of the end liquid sample do not allow it to be used to prepare samples for analysis by biochemical or biological analysis techniques.

Also known from Otaki et al. (Wat. Sci. Tech. 37, 10, 107–116, 1998), for the validation of the performance of microfiltration membranes, is the continuous and tangential-mode use of a device for ultrafiltration on hollow fibers, with the analysis of withdrawal performed periodically by withdrawing samples from the supply, the filtrate and the concentrate respectively.

The use of tangential-mode filtration and ultrafiltration means entails the presence of a circuit allowing all or some of the concentrate to be recirculated in order to maintain a tangential velocity at the membrane to allow particles in suspension to be filtered while at the same time avoiding swift clogging of the membranes used ("Microfiltration and Ultrafiltration—Principles and Applications", Leos J. Zeman, Andrew L. Zydney, Marcel Dekker, Inc. New York-Basle-Hong Kong 1996).

The recirculation of the fluids subjected to the filtration induces lengthened filtration times and, above all, additional volumes in which some of the concentrate and microorganisms cannot be collected without an impact on the end volumes.

The high volumes of concentrate which are due to the volume of the pipework and also to the volume of eluent needed to extract the microorganisms which may have remained on the walls, and the lengthening of the filtration time, make these techniques incompatible with analysis means entailing small volumes for analysis and which allow results to be obtained quickly, for example to respond to queries over the contamination of drinking water or any other fluid intended for human consumption.

The object of the invention is the use of a filtering means making it possible, in a limited length of time, to obtain, from a large- and predetermined-volume starting liquid sample, a sample for analysis the volume of which is small enough that biochemical or biological analysis techniques, particularly immunoassay and molecular biology techniques, for example for multidetection, can then be carried out while at the same time guaranteeing the viability of the microorganisms.

The filtering means used according to the invention is based on the technique of ultrafiltration over hollow fibers in frontal mode.

Frontal mode, as opposed to tangential mode, is to be understood as meaning any single-pass passing of the starting liquid sample through the filtering means without at least some of the same sample being recycled to the inlet of said filtering means.

The use of this frontal-mode ultrafiltration means makes it possible to obtain small-volume concentrates, to concentrate a sample in a timescale of the order of one hour at the most in a single pass, while at the same time guaranteeing the viability of the microorganisms, multiple collection and yields of the order of 100%.

The expression "multiple collection" is to be understood as meaning the possibility of collecting, from the end sample, practically all the different kinds or species of microorganism present in the starting sample.

These high yields are obtained because of the fact that there are no volumes known as dead volumes due, for example on other devices, to the presence of auxiliary pipework, for example recycling pipework, and due to the reliability of the porosity along the entire length of the hollow fiber.

The characteristics of the filtering means used will become apparent from reading the description given with reference to the appended drawing in which FIG. 1 schematically and in longitudinal section depicts a filtering means according to the invention and FIG. 2 depicts a view in cross section, on an enlarged scale, of the same filtering means. The size of the fibers has deliberately been exaggerated to make the invention understandable.

The filtering means comprises a housing (2) in which there are arranged, parallel to one another, a plurality of hollow fibers (3), the porous wall (3a) of each of which determines an aperture (4) so that said means comprises an internal path (A) consisting of the plurality of the parallel apertures (4) of said respective hollow fibers and an external path (B) corresponding to the volume available between the fibers and the housing.

According to the invention, this means is used for treating a starting liquid sample of large volume comprising, in the dilute state, a plurality of microorganisms of different sizes, to obtain a final liquid sample of small volume, comprising, in the concentrated state, the same composition of microorganisms.

When this means is in use, at least one concentrating step is performed in which:

a) use is made of a single filtering means b) said filtering means is used in frontal mode, c) the cut-off threshold of the porous wall (3a) of the fibers is determined so as to retain the smallest-sized microorganism of the starting sample, and, discontinuously:

d) during a filtering phase, all of the starting liquid sample is introduced through one of the paths (A, B) of the filtering means, a filtrate is removed via the other of the paths (B, A) of the filtering means, and a concentrate is accumulated in said path via which the liquid sample was introduced, e) during a collection phase, having passed all of the sample, passage of the starting liquid sample through the filtering means (1) from said path to said other path is halted and the outlet liquid sample, from the concentrate, is obtained.

The outlet liquid sample formed by the concentrate can be collected either simply under gravity or by the use of a compressed gas or by physical agitation of said filtering means, but can also be collected by elution with any appropriate substance, for example in the case of microorganisms using a saline solution of PBS type (eg: 120 mmol NaCl, 2.7 mmol KCl, 10 mmol $NaH_2PO_4$) possibly containing a detergent of the TWEEN 20 type and/or a surfactant of the BSA (Bovine Serum Albumin) type.

According to another embodiment, the outlet liquid sample formed by the concentrate is subjected to a second concentrating step and then in this second concentrating phase constitutes the starting liquid sample.

The walls of the hollow fibers (3a) may be made of any material allowing the manufacture of hollow fibers of defined porosity, such as organic membranes, for example made of cellulose acetate, ethylcellulose, polyether sulfone, or polyacrylonitrile, or inorganic membranes, for example a ceramic.

The cut-off threshold for the porous wall (3a) of the fibers is determined so as to retain the smallest-sized microorganism of the starting sample. Use will therefore be made of fibers with a porosity of 10 to 100 nm, for the ultrafiltration domain, so that the concentrate will contain all the microorganisms of a size exceeding that of viruses, including the latter, but if the size of the sought particles so demands, particularly in the case of particles smaller than 10 nm, fibers with a porosity of 1 to 10 nm for the nanofiltration domain may be used.

According to one embodiment, the path via which the starting sample is introduced is the internal path (A) and the path via which the outlet sample is extracted is the external path (B), so that the microorganisms accumulate inside the fibers to form the concentrate while the filtrate passes along the outside of the fibers in the volume available between the fibers and the housing (B).

The sample to be treated consisting of a withdrawn sample of water with a volume of for example from 10 to 100 liters is introduced by a valve (C) into the hollow fibers of the module, carried along for example by suction exerted by a peristaltic pump or any other means, such as a depression created on the filtrate side by the valve (E), the valves (D) and (F) remaining closed.

When all of the volume to be treated has passed through the module, the pump is stopped, the valve (C) is closed and disconnected from the source of sample.

The housing is then emptied to remove the filtrate, for example via the valve (F), by placing the module at atmospheric pressure, for example by opening the valve (E), then by pressurizing it, for example to 0.5 bar of compressed air, the valve (E) then being closed again.

The concentrate is then collected via the valve (D) by opening the valve (C), to start with under gravity and then ending with the closure of the valve (C) and the injection of compressed air into the fibers.

According to another embodiment, the path via which the starting sample is introduced is the external path (B) and the path via which the outlet sample is extracted is the internal path (A), so that the microorganisms accumulate on the outside of the fibers in the volume available between the fibers and the housing to form the concentrate, and so that the filtrate passes along inside the fibers to be removed.

The sample to be treated consisting of a withdrawn sample of water with a volume of for example from 10 to 100 liters is introduced, via the valve (E) into the housing, carried along for example by a depression, which may be created by suction performed by a peristaltic pump or any other means, a depression created on the filtrate side inside the hollow fibers for example by the valve (D), the valve (C) remaining closed.

When all of the volume to be treated has passed through the module, the pump is kept running, the valve (E) being disconnected from the source of sample to reduce the volume of concentrate contained in the housing of the module; this reduction may be complete or partial.

When the level of concentration for the desired concentrate is reached, the pump is stopped and the valve (D) is closed together with all the valves.

A solution of eluent is possibly introduced into the housing, then the module is agitated and the concentrate or the eluate is then collected via the valve (F), possibly ending with the injection of compressed air through the valve (E).

In order to limit adsorption phenomena, the fibers may have been treated beforehand for example with a detergent of the TWEEN type and/or with a surfactant of the BSA (Bovine Serum Albumin) type.

According to one embodiment, the filtering phase (C) is performed without prefiltration of the starting liquid sample, if the suspended matter content of the fluids for analysis so permits.

In the case of the method of introduction via the internal path (A), the volume of the concentrate obtained is linked directly to the size of the filtration means; for the method of introduction through the external path (B), the volume of said concentrate does not depend on the size of the filtration means but on the volume left in the housing and/or on the volume of eluent introduced into this housing.

The filtering means will be sized so that the ratio between the volume of the starting sample and the volume of the concentrate obtained is at least equal to 50 and preferably between 150 and 500, with a filtration time of between 20 minutes and one hour.

If the application so permits, the module can be reused after having been backwashed or having undergone a treatment with a decontaminant, for example a 50 ppm chlorine solution possibly associated with an enzyme treatment.

There are two methods of backwash that can be employed depending on whether the path via which the sample is introduced is the internal path (A) or the external path (B), the washing water being introduced against the current of the introduction of the sample for analysis.

When the path via which the sample is introduced is the internal path (A), through the valve (C), backwashing is performed by introducing mains water through the valve (F) using a delivery means, such as a peristaltic pump placed between the source of water and said valve, the valve (D) being closed and the valve (E) temporarily remaining open.

When the housing is full, the valve (E) is closed and the water is forced to pass along the inside of the fibers to leave via the valve (C) or (D).

When the path via which the sample is introduced is the external path (B), backwashing is performed by introducing mains water through the valve (D), the valves (E) and (F) being closed.

When the fibers are full of water, that is to say when air bubbles are no longer seen leaving the valve (C), this valve is closed and the water is forced to pass around the outside of the fibers in the housing to leave via the valve (E) or the valve (F).

Single use of the module could possibly be anticipated, as could initial sterility of the module by gamma-ray sterilization treatment for example.

In another embodiment, use may be made of a seal-free module, as this avoids any risk of external contamination (fluid external to the module such as the surrounding air); this also avoids any passage across the seals of contaminants from the concentrate to the filtrate. Sealing is achieved by embedding the hollow fibers in a resin at their two respective ends, as depicted in FIG. 1, and any leak of contaminant is thus prevented, something which is not the case with systems that have seals.

In another embodiment, to obtain a volume of concentrate compatible with the analysis methods employed, the concentrate obtained can be subjected to a second concentrating step.

In this second concentrating step, the filtering means used may be of the same configuration as the one used in the first step but of smaller volume, calculated according to the ratio between the starting volume and the desired volume of concentrate.

As the volumes treated are of the order of one hundredth of a ml, known means such as filtering devices resorting to centrifugal separation techniques such as the devices marketed by Millipore under the name Centricon-Plus 80 can be used.

These filtering means are dimensioned and the treatments are performed for a length of time determined such that the ratio between the volume of the starting sample and the volume of the end sample is at least equal to 5000 and preferably between 15,000 and 100,000.

The use of the filtering means according to the invention therefore exhibits the advantages of allowing multiple collection with a yield close to 100% of the microorganisms present in large volumes of liquid for analysis, of guaranteeing the viability of the microorganisms thus collected, of performing this multiple collection in times of the order of one hour at most, compatible with the requirements, for example, of continuous health monitoring, and of obtaining volumes of concentrate for analysis that allow biochemical or biological analysis techniques, particularly immunoassays and molecular biology techniques, to be employed.

The following examples provide a nonlimiting illustration of the use of a filtering means according to the invention:

EXAMPLE 1

Equipment and Method:

Use of a filtering means comprising 1 m² of filter area made up of hollow cellulose acetate fibers.

The sample consisting of 50 liters of mains water doped with the MS2 bacteriophage is introduced via the internal path;

the concentrate is collected under gravity and under pressure;

the concentrate is analyzed using the lysis plaque technique measuring both the viability and the infectiousness of the bacteriophage, either quantitatively (after serial ten-fold dilutions of the sample) or qualitatively (after biological amplification by infection of an MS2-sensitive bacterial culture).

Procedure:

The inocula are sonicated prior to doping and withdrawal of a sample of tap water in a tank so as to disaggregate the viral particles.

Following the addition of 20 mg/l of sodium thiosulfate (STS (Merck 106516)), namely 1 g in 50 l, the sample is doped with MS2.

One filtration cycle is performed then the housing is emptied, sealed and placed under air pressure (0.5 b). Next, the concentrate is collected under gravity. Compressed air (0.5 b) is then also injected into the fibers to collect the last milliliters of concentrate that have remained in the fibers.

The count is then performed using the lysis plaque technique with *Escherichia coli* (*E. coli*) Hfr sensitive strain, sonicating the concentrates beforehand.

Preparation of the Inocula:

| MS2 dilution | MS2 dilution volume | SPW | Final titer (PFU/ml) |
|---|---|---|---|
| Stock | — | — | $2.10^8$ |
| $I10^7$ | 500 µl stock | 9.5 ml | $10^7$ |
| $I10^6$ | 1 ml of $I10^7$ | 9 ml | $10^6$ |
| $I10^5$ | 1 ml of $I10^6$ | 9 ml | $10^5$ |
| $I10^4$ | 1 ml of $I10^5$ | 9 ml | $10^4$ |
| $I10^3$ | 1 ml of $I10^4$ | 9 ml | $10^3$ |
| I100 | 1 ml of $I10^3$ | 9 ml | 100 |
| I10 | 1 ml of I100 | 9 ml | 10 |
| I1 | 1 ml of I10 | 9 ml | 1 |

SPW = Saline Peptone Water; PFU = Plaque Forming Unit (infectious viral unit); $I10^x$ = inoculum containing $10^x$ PFU per ml.

Filtration:

50 liters of STS-neutralized tap water are filtered and, having emptied the housing, a concentrate is collected which will constitute a blank=blank 1 (B1).

After backwashing to clean the membrane 50 liters of STS-neutralized tap water are filtered and, after emptying the housing, a concentrate is collected which will constitute a blank=blank 2 (B2).

After backwashing to clean the membrane, 50 liters of tap water are neutralized with STS.

After a waiting time of 15 minutes, one liter is drawn off to dilute the inoculum intended for the tank.

Doping is performed using 1 ml of I10 (10 PFU) diluted in 1 liter.

After one filtration cycle, the concentrate is collected (C10);

a backwashing is performed.

In this example, the backwashings are performed with at least 20 liters of water.

The same procedure is then repeated, doping with 1 ml of $I10^4$ ($10^4$ PFU). The withdrawal of a sample of filtrate during filtration gives the sample (F). At the end of filtration the concentrate is collected ($C10^4$);

doping a 100 ml fraction of B1 with 1 ml of $I10^4$ ($10^4$ PFU) gives the doped blank control sample ($BD10^4$);

Analysis:

quantitative titration of I100, I10, I1, $C10^4$, $BD10^4$.

The aliquots of each pure sample and the inocula are taken in a test tube and subjected to sonication before the dilutions are performed.

The infectious particles are counted using the lysis plaque technique using the following procedure:

2 ml of a molten (44° C.) soft Top Agar (0.95%) are mixed with 1 ml of viral suspension and 0.3 ml of *E. coli* Hfr culture in the exponential growth phase. The combination is quickly and gently mixed then poured over the entire surface of a hard nutrient agar in a Petri dish. After incubation at 37° C., the lysis plaques are read the following day.

Results Obtained:

| Dilutions | Counts | | | | Means | Standard deviations | Overall mean | Comment |
|---|---|---|---|---|---|---|---|---|
| I 100 | 61 | 78 | 74 | 75 | 72.0 | 6.5 | 74.5 | |
| I 10 | 9 | 7 | 17 | 8 | 10.3 | 4.0 | | |

| | Total volume | Volume of sample (ml) | PFU expected/ sample | Qualitative test | | | | | | Partial evaluation (PFU/vol) | Extrapolation (PFU/ PFU) |
|---|---|---|---|---|---|---|---|---|---|---|---|
| B2 | 325 | 25 | 0 | | | N | | | | 0 | na |
| | | 50 | 0 | N | N | N | N | N | N | 0 | na |
| F | 50 | 50 | 0 | | | N | | | | 0 | na |
| C10 | 302 | 6 | 1 | | | N | | | | 0/6 ml | 4–6/10 |
| | | 50 | 1.5 | P | P | P | P | N | N | 4–6/ 300 ml | |
| T+ | Na | na | na | P | P | P | P | P | P | Na | na |

N = negative;
P: positive;
na: not applicable

-continued

| Dilutions | Counts | | | | Means | Standard deviations | Overall mean | Comment |
|---|---|---|---|---|---|---|---|---|
| I 1 | 1 | 1 | 0 | 0 | 0.5 | 0.5 | | |
| C$10^4$ pure | 14 | 13 | 15 | *6 | 14.0 | 0.8 | 13.9 | *6 set aside: readings dubious |
| C$10^4$ $10^{-1}$ | 1 | 3 | 1 | 0 | 1.3 | 1.1 | | |
| BD$10^4$ $10^{-1}$ | 61 | 81 | 60 | 78 | 70.0 | 9.6 | 78.2 | |
| BD$10^4$ $10^{-2}$ | 13 | 19 | 14 | 18 | 16.0 | 2.5 | | |

C$10^4$ $10^{-1}$, for example, denotes the 1/10 dilution of the concentrate obtained from the sample doped with $10^4$ PFU.

| | Volume (ml) | Expected titer (PFU/ml) | Titer obtained (PFU/ml) | Expected quantity (PFU) | Quantity obtained (PFU) | Obtained/ expected |
|---|---|---|---|---|---|---|
| I $10^4$ | — | 1.E+04 | 7.45E+03 | — | — | 74.5% |
| C $10^4$ | 325 | 31 | 14 | 1.E+04 | 4506 | 45.1% |
| BD $10^4$ | 100 | 1.E+02 | 78 | 1.E+04 | 7818 | 78.2% |

C = 45.1%
C/BD = 56.7%
C/I = 60.4%

Qualitative Test:

Detection of the presence or absence of phage on I$10^7$ (positive control=T+), F (1 50 ml sample), B2 (6×50 ml+remainder to cover the entire sample), C10 (6×50 ml+remainder to cover the entire sample).

One volume of sample is mixed with one volume of two-times concentrated nutrient broth. After incubating for 30 minutes at 37° C., it is inoculated with an *E. coli* Hfr culture in the exponential phase. After incubation overnight at 37° C. (viral multiplication phase), an exponential culture of *E. coli* Hfr is plated out on nutrient agar in a Petri dish and left to dry. Drops of viral amplification broth are deposited and left to incubate for at least six hours at 37° C.

The presence of infectious particles is revealed by the presence of lysis plaques more or less confluent at the point of drop deposition.

In the event of the absence of infectious particles, the growth of *E. coli* Hfr produces a thick layer of cells at the location of the deposition.

Interpretation of the Results:

The blank (B2) contains no infectious bacteriophage: the module is therefore not contaminated beforehand with MS2 and the concentrating of the 10 PFU, performed later, is valid.

The sample of the filtrate (50 ml) taken during the concentrating of the $10^4$ PFU contains no detectable MS2: the membrane therefore effectively retains this virus which measures 25 nm in diameter.

As four infectious units were detected in C10, the detection threshold is therefore lower than 10 PFU.

The actual yield (that is to say related to the measured titer of the inoculum: C/I) is 60% for a doping of $10^4$ PFU in the absence of any particular collection method (no agitation and no elution) and bearing in mind the viability because the measurement relates to the infectiousness of the bacteriophage.

The ratio C/BD is very close to the actual yield, which demonstrates that there is no interference due to the concentrate.

EXAMPLE 2

Equipment and Method:

Use of a filtering means comprising 0.6 m² of filter area made of cellulose acetate hollow fibers.

The sample consists of 50 liters of mains water doped with oocysts of the parasite *Cryptosporidium parvum*. It is introduced by the external path.

The concentrate is collected by agitation and collection under gravity and under pressure.

Analysis is performed using the IMS-IFA: ImmunoMagnetic Separation—ImmunoFluorescence Assay technique (see standardized method 1622—EPA-EPA-821-R-99-001 from the US Environment Protection Agency) using the Dynal anti-Cryptosporidium Dynabeads kit, ref. 730.01 (respecting the integrity of the oocysts).

Procedure:

Having taken tap water in the tank, 20 mg/l of sodium thiosulfate (STS (Merck 106516)) are added, namely 1 g to 50 l;

the sample is doped with the oocysts of C. parvum;

filtration is performed using the external path method;

after partial emptying of the housing and agitation of the module to collect all the oocysts on the external surface of the fibers by virtue of the liquid left in the housing, the concentrate is collected under gravity then by injecting compressed air (0.5 b) into the housing.

The stock of oocysts and of the concentrate are counted using IMS-IFA.

Filtration:

Method:

50 liters of STS-neutralized tap water are filtered and, after emptying, a concentrate is collected which will constitute a blank (B); this filtration is followed by a backwashing to clean the membrane;

50 liters of tap water are then neutralized with STS then doped with a I10 dilution of the oocyst stock (namely about 10 oocysts).

After filtration, emptying is performed and a concentrate is collected (C10);

this filtration is followed by backwashing with at least 10 liters of water.

The same procedure is then repeated, doping with I100 (approximately 100 oocysts), yielding the concentrate C100, then doping with I1000 (approximately 1000 oocysts) to obtain the concentrate C1000;

Analysis:

I10, I100, I1000, B, C10, C100 and C1000 count using IMS/IFA.

Results:

| Inoculum | | Concentrates | | Yield |
|---|---|---|---|---|
| — | — | B | 0 | — |
| I10 | 4 | C10 | 15 | ≈ 100% |
| I100 | 43 | C100 | 57 | ≈ 100% |
| I1000 | 335 | C1000 | 236 | 70% |

The results for C10 and C100 which are higher than the value measured for the inoculum should not give cause for surprise: the sampling for counting the oocysts under the microscope of necessity entails fluctuations, as can be seen when the counts from one and the same sample are multiplied. This phenomenon is more pronounced when the oocysts are rare.

Thus, for C10 and C100, it must be considered that the order of magnitude after filtration is constant.

For C1000, it is possible to speak of yield.

Interpretation of the Results:

The method of filtration by the external path has a sensitivity of 10 oocysts or less.

For an inoculum of 1000 oocysts, the yield obtained is 70% without optimization.

EXAMPLE 3

The procedure and the method used are identical to those used in Example 1, except for the filtering means.

Filtration is performed using a filtering means comprising 0.6 $m^2$ of filtering area made of cellulose acetate hollow fibers.

The sample consists of 50 liters of mains water doped with the MS2 bacteriophage; it is introduced by the internal path (A).

The concentrate is collected under gravity and under pressure.

Just one blank ($B_1$) is produced, and doping is performed with 1, 10 and 100 PFU in succession.

Analysis is performed by the lysis plaque technique as in Example 1.

A second step of filtering the concentrates resulting from the preceding filtration exercise was carried out in accordance with the procedure described below.

The blank concentrate ($B_1$) and each of the phage concentrates ($C_1$1, $C_1$10, $C_1$100), namely about 230 ml each, are split into three equal fractions (70–80 ml) for a second concentration in three commercial Centricon-Plus 80 modules (Millipore ref. UFC5LGC08).

The three concentrates $C_2$ thus obtained (<1 ml) for each doping are mixed and analyzed in quantitative titration by lysis plaques. The same procedure is followed for the three blank concentrates ($B_2$) originating from the concentration of $B_1$.

Results:

titration of the inoculum: I100=144 PFU (overall mean as in Example 1);

titration of the concentrates obtained after the second filtration:

| | Titer read (PFU) | Inoculum (PFU) |
|---|---|---|
| $B_2$ | 0 | 0 |
| $C_2$1 | 2 | 1.44 |
| $C_2$10 | 8 | 14.4 |
| $C_2$100 | 61 | 144 |

$C_2$1, for example, denotes the mixture of the three concentrates obtained at the end of the second step of concentrating the initial sample doped with 1 PFU.

Interpretation of the Results:

Across the two concentration steps taken together, reducing the volume of the sample from 50 liters to under 3 ml, sensitivity is close to 1 PFU.

Of course, the present invention is not restricted to the exemplary embodiments described and/or depicted, but encompasses all alternative forms which fall within the scope of the attached claims (particularly as regards the nature and the characteristics of the membranes used to concentrate the samples).

EXAMPLE 4

Equipment and Method:

Use of a filtering means comprising 0.12 $m^2$ of filtering area made of cellulose acetate hollow fibers for a first filtering phase and of a Vivacell70consumable (Sartorius Vivasciences ref. VS6002) for a second filtering phase.

The sample consists of 30 liters of mains water doped simultaneously with 300 oocysts of the parasite *Cryptosporidium parvum* and 300 CFU of the bacterium *Escherichia coli.*

Concentration:

Having taken tap water in the tank, 20 mg/l of sodium thiosulfate (Merck 106516) are added, namely 0.6 g to 30 l;

the sample is doped with the oocysts of *C. parvum* and the *E. coli* cells;

Phase 1: from 30 Liters to 70 ml

Filtration is performed using the external path mode.

After partial emptying of the housing and agitation of the module, the retentate containing the microorganisms is collected by injecting compressed air (0.5 b) into the housing, namely about 35 ml.

Undoped neutralized mains water is reintroduced into the housing (about 35 ml) through the fibers by injection into the closed internal compartment, then agitation and collection are performed as previously.

The combination of the two collected samples, namely 70 ml, constitutes the retentate R1.

Phase 2: from 70 ml to 300 Microliters

The retentate R1 is concentrated in the Vivacell70 consumable as indicated by the supplier, applying a centrifugal force of 1000 G for 10 min at 25° C. To improve collection, 1 ml of filtrate is applied to the concentrate in the filtration chamber, then the filtrating element is "vortexed" briefly at high speed. A further centrifuging operation under the same conditions as before allows reconcentration to a maximum of 300 microliters. This then yields the final retentate R2.

Three retentates R2 are produced in parallel to triplicate the results.

Analyses:

Search for C. parvum:

The stock of oocysts and a fraction of the retentate are counted by IMS (ImmunoMagnetic Separation—Dynal anti-Cryptosporidium Dynabeads kit, ref. 730.01) followed by IFA (ImmunoFluorescence Assay), (see Method 1622).

A fraction of the retentate is analyzed by IMS (see above) then PCR according to the following procedure:
take up the beads/oocysts complex from the IMS in 10 µl of ultrapure sterile water+10 µl of 50% Chelex-100 in water;
apply 5 thermal shocks: 2 min at 95° C./2 min at −80° C.; centrifuge to pellet the condensation;
add 30 µl of amplification mix (PCR buffer, MgCl$_2$: 1.5 mM, Bovine Serum Albumin: 10 pg/µl, dNTP: 200 pmol/µl, Taq DNA polymerase: 0.5 U, primers BB-3 and BB-4: 1 pmol/µl of each, ultrapure water to make up to 50 µl).

The primers BB-3 and BB-4 are described in Balatbat A. B. et al. J. Clin. Microbiol. 1996, 34, 1769–1772.

Apply the following PCR program: 5 min at 94° C., 40 cycles comprising: [30 sec at 94° C., 45 sec at 60° C., 1 min at 72° C.] then 5 min at 72° C.

Migrate 10 µl of PCR reaction on an electrophoresis gel containing 2% agarose in the presence of ethidium bromide.

Search for E. coli:

The E. coli culture and a fraction of the retentate is counted using the "Colilert 18h" technique in accordance with the IDEXX supplier recommendations. This method is based on the detection of beta-glucuronidase activity of Escherichia coli.

A fraction of the retentate is analyzed by nested PCR applied to the uidA gene which codes for beta-glucuronidase according to the following procedure:
filter the concentrate fraction on a membrane (Millipore, diameter 13 mm, porosity 0.2 µm by Durapore GVWP013 00);
insert the membrane into a 0.2 ml PCR tube;
lyze the cells by thermal shock (6 cycles 85° C. 1 min/ice 1 min)
first amplification in the lysis tube using primers U270 and L1054
U270: 5'-ggT CAC TCA TTA Cgg CAA Ag-3' (SEQ ID NO:1)

L1054: 5'-TTA Aag CCg ACA gCA gCA gT-3' (SEQ ID NO:2)

Amplification mix (150 µl) placed in the PCR tube containing the membrane: PCR buffer, MgCl$_2$: 1.5 mM, dNTP: 200 pmol/µl, Taq DNA polymerase: 1.5 U, primers: 1 pmol/µl of each, ultrapure water to make up to 150 µl.

PCR program: 10 min at 95° C., 30 cycles comprising: [1 min at 94° C., 1 min at 60° C.] then held at 4° C.

dilute the amplicons obtained 100 times in ultrapure water and use 1 µl of this dilution as substrate for the second amplification (known as nested PCT) with the primers Val 754 and Val 900:
Val 754: 5'-AAA Acg gCA AgA AAA AgC Ag-3' (SEQ ID NO:3)
Val 900: 5'-Acg CgT ggT TAC AgT CTT gCg-3' (SEQ ID NO:4)

Amplification mix (50 µl) placed in a fresh tube: PCR buffer, MgCl$_2$: 1.5 mM, dNTP: 200 pmol/µl, Taq DNA polymerase: 0.5 U, primers: 1 pmol/µl of each ultrapure water to make up to 50 µl.

PCR program: same as before.

migrate 10 µl of PCR reaction onto electrophoresis gel containing 2% agarose in the presence of ethidium bromide.

Treatment of the Retentate R2:

The retentate is split into three fractions of 100 microliters each: R2a, R2b, R2c.

Fraction R2a is split into two again: 50 µl are treated using the "Colilert 18h" procedure (E. coli count), and 50 µl are treated by IMS-IFA (for the C. parvum count).

Fraction R2b is analyzed by uidA nested PCR (molecular detection of E. coli) but before that it is split into two: 50 µl are analyzed directly, 50 µl have E. coli genomic DNA added to them (inhibition test).

Fraction R2c is analyzed by IMS-PCR (molecular detection of C. parvum) but before that it is split into two: 50 µl are analyzed directly, 50 µl have C. parvum genomic DNA added to them (inhibition test).

The PCRs each have a negative control (no target DNA and no retentate) and a positive control (with target DNA but no retentate).

All the amplicons are viewed on agarose gel by electrophoresis in the presence of ethidium bromide.

Results:

Each point is reproduced three times and the repeated results are separated by the symbol "/" in the table below.

|  | Theoretical count in the fraction analyzed | Result (count or band on gel) |
|---|---|---|
| E. coli count (Colilert) | 50 | 0/1/2 |
| E. coli uidA nested PCR detection | 50 | +/+/+ |
| uidA PCR inhibition test | 50 | +/+/+ |
| uidA PCR positive control | 50 | + |
| uidA PCR negative control | 50 | − |
| C. parvum count (IMS-IFA) | 50 | 1/11/9 |
| C. parvum IMS-PCR detection | 50 | +/+/+ |
| C. parvum IMS-PCR inhibition test | 50 | +/+/+ |
| C. parvum IMS-PCR positive control | 50 | + |
| C. parvum IMS-PCR negative control | 50 | − |

Interpretation of the Results:

The low number of E. coli cells detected by Colilert in the concentrate can be explained by the stress, or even the mortality, experienced by the bacteria during concentration because this test is based on the detection of enzyme activity.

The uidA PCR is positive for the three repeats, which indicates a repeatable sensitivity of the method as a whole of 50 bacteria in 5 liters, namely 5 bacteria per liter.

CONCLUSION

This example demonstrates the effectiveness of the two-step concentration device for detecting, in one and the same doped water sample, a bacterium and a parasite using molecular biology methods.

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
ggtcactcat tacggcaaag                                               20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
ttaaagccga cagcagcagt                                               20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
aaaacggcaa gaaaaagcag                                               20

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
acgcgtggtt acagtcttgc g                                             21
```

Logically, the addition of bacterial DNA to a fraction as an inhibition control also gives positive responses. In the case of C. parvum, the phenotype method (IMS-IFA) give significantly lower counts than the expected theoretical value. Here again, it is probable that some of the oocysts were adversely affected during concentration rather than retained in the filtration device because other experiments based on molecular biology indicate a repeatable collection of 1 oocyst in 10 liters (data not disclosed in this patent).

Incidentally, the IMS-PCR is positive for the three repeats, which gives a minimum sensitivity of 50 oocysts in 5 liters, namely 5 oocysts per liter.

The invention claimed is:

1. A method of filtering with a filter comprising a housing (2) in which there are arranged, parallel to one another, a plurality of hollow fibers (3), the porous wall (3a) of each of which determines an aperture (4) so that said means comprises an internal path (A) consisting of the plurality of the parallel apertures (4) of said respective hollow fibers and an external path (B) corresponding to the volume available between the fibers and the housing, for treating a starting liquid sample of large volume comprising, in the dilute state, a plurality of microorganisms of different sizes, to obtain a final liquid sample of small volume, comprising, in the concentrated state, the same relative composition of microorganisms, said method comprising, during at least one concentrating step, the steps of:
   a. using a single filtering means
   b. using said means in frontal mode,
   c. determining the cut-off threshold of the porous wall (3a) of the fibers, so as to retain the smallest-sized microorganism of the starting sample, and, discontinuously:
   d. introducing during a filtering phase, all of the starting liquid sample through the internal path (A) of the filtering means, removing a filtrate via the external path (B) of the filtering means, and accumulating a concentrate in said path via which the liquid sample was introduced,
   e. during a collection phase, having passed all of the starting liquid sample, halting the passage of this sample through the filtering means (1) from said path to said other path and obtaining the outlet liquid sample, namely the concentrate,
   f. circulating during a backwash phase, a liquid flow which may be free of microorganisms from said path to said other path.

2. A method of filtering with a filter comprising a housing (2) in which there are arranged, parallel to one another, a plurality of hollow fibers (3), the porous wall (3a) of each of which determines an aperture (4) so that said means comprises an internal path (A) consisting of the plurality of the parallel apertures (4) of said respective hollow fibers and an external path (B) corresponding to the volume available between the fibers and the housing, for treating a starting liquid sample of large volume comprising, in the dilute state, a plurality of microorganisms of different sizes, to obtain a final liquid sample of small volume, comprising, in the concentrated state, the same relative composition of microorganisms, said method comprising, during at least one concentrating step the steps of:
   a. using a single filtering means
   b. using said means in frontal mode,
   c. determining the cut-off threshold of the porous wall (3a) of the fibers so as to retain the smallest-sized microorganism of the starting sample, and, discontinuously:
   d. introducing during a filtering phase, all of the starting liquid sample through the external path (B) of the filtering means, removing a filtrate via the internal path (A) of the filtering means, and accumulating a concentrate in said path via which the liquid sample was introduced,
   e. during a collection phase, having passed all of the starting liquid sample, halting the passage of this sample through the filtering means (1) from said path to said other path and obtaining the outlet liquid sample, namely the concentrate.

3. The method as claimed in claim 1, characterized in that, between the filtering phase (d) and the collection phase (e), the external path is empty and possibly pressurized with air.

4. The method as claimed in claim 1, characterized in that the collection phase (e) is performed under gravity flow of the concentrate and/or by passing pressurized air into the internal path.

5. The method as claimed in claim 1, characterized in that it comprises, during the filtering phase (d), a step of circulating the starting liquid sample through the internal path by delivery to the inlet of the internal path and/or suction at the outlet of said internal path.

6. The method as claimed in claim 2, characterized in that it comprises, during a backwash phase, a step of circulating a liquid flow which may be free of microorganisms from said path to said other path.

7. The method as claimed in claim 2, characterized in that it comprises, between the filtering phase (d) and the collection phase (e), a step of emptying the external path is partially or completely.

8. The method as claimed in claim 2, characterized in that it comprises a step of obtaining the end liquid sample by elution of the concentrate in the external path.

9. The method as claimed in claim 1, characterized in that the filtering phase (d) is performed without prefiltration of the starting liquid sample.

10. The method as claimed in claim 1, characterized in that the filtering means is an ultrafiltration means.

11. The method as claimed in claim 1, characterized in that the fibers of the filtering means consist of an organic membrane or of an inorganic membrane.

12. The method as claimed in claim 1, characterized in that the hollow fibers of the filtering means are embedded at their two respective ends in a resin to prevent any passage of contaminant between the internal path (A) and the external path (B) and between the filtering means and the outside.

13. The method as claimed in claim 1, characterized in that the filtering means is sized and the filtering phase is performed for a length of time determined such that the ratio between the volume of the starting sample and the volume of the end sample is at least equal to 50.

14. The method as claimed in claim 1, characterized in that at least two successive steps of concentrating a liquid sample are performed, these two steps being performed by using the filtering means, the concentrate obtained at the end of the first concentrating step constituting the starting liquid sample for the second concentrating step.

15. The method as claimed in claim 1, characterized in that at least two successive treatments are performed on a liquid sample, and at least one of these treatments being the concentrating step, the concentrate obtained at the end of the first treatment constituting the starting liquid sample for the second treatment.

16. The method as claimed in claim 11, characterized in that the organic membrane is made of cellulose acetate, ethyl cellulose, polyether sulfone, or polyacrylonitrile.

17. The method as claimed in claim 11, characterized in that the inorganic membrane is made of ceramic.

18. The method as claimed in claim 1, characterized in that the ratio between the volume of the starting sample and the volume of the end sample is comprised between 150 and 500.

19. The method as claimed in claim 18 characterized in that the ratio between the volume of the starting sample and the volume of the end sample is comprised between 15,000 and 100,000.

20. The method as claimed in claim 16, characterized in that the filtering means are dimensioned and the treatments are performed for a length of time determined such that the ratio between the volume of the starting sample and the volume of the end sample is at least equal to 5000.

* * * * *

UNITED STATES PATENT AND TRADEMARK OFFICE
CERTIFICATE OF CORRECTION

PATENT NO. : 7,179,636 B2  Page 1 of 1
APPLICATION NO. : 10/297769
DATED : February 20, 2007
INVENTOR(S) : Emmanuelle Guillot, Laurence Durand Bourlier and Stephane Bulteau It is certified that error appears in the above-identified patent and that said Letters Patent is hereby corrected as shown below:

Please correct the title page as follows:

(75) Inventors: Emmanuelle Guillot, Saint Germain en Laye (FR); Laurence Durand-Bourlier, Clamart (FR): Stephane Bulteau, Lyon (FR)

Signed and Sealed this

Nineteenth Day of February, 2008

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,179,636 B2 |
| APPLICATION NO. | : 10/297769 |
| DATED | : February 20, 2007 |
| INVENTOR(S) | : Emmanuelle Guillot, Laurence Durand Bourlier and Stephane Bulteau |

It is certified that error appears in the above-identified patent and that said Letters Patent is hereby corrected as shown below:

Title Pg, insert Item (30) as follows:

-- (30)  Foreign Application Priority Data
   Jun. 9, 2000     (FR)    00/07459 --.

Signed and Sealed this

Thirty-first Day of March, 2009

JOHN DOLL
*Acting Director of the United States Patent and Trademark Office*